United States Patent [19]

Seib et al.

[11] 4,085,264

[45] Apr. 18, 1978

[54] PROCESS FOR PREPARING COPOLYMERS OF ACRYLIC ACID OR METHACRYLIC ACID AND ACRYLIC AND METHACRYLIC ACID ESTERS

[75] Inventors: Karl Seib, Weinheim; Wolfgang Schwarz, Ludwigshafen; Hermann Gausepohl, Mutterstadt, all of Germany

[73] Assignee: BASF Aktiengesellschaft, Ludwigshafen, Germany

[21] Appl. No.: 784,569

[22] Filed: Apr. 4, 1977

[30] Foreign Application Priority Data

May 15, 1976 Germany .............................. 2621722

[51] Int. Cl.$^2$ ...................... C08C 19/00; C08C 19/22; C08F 20/04; C08F 220/04
[52] U.S. Cl. ........................................ 526/47; 427/47; 526/16; 526/49; 526/227; 526/317
[58] Field of Search .................... 526/317, 16, 47, 49; 424/47

[56] References Cited

U.S. PATENT DOCUMENTS

| | | | |
|---|---|---|---|
| 2,790,736 | 4/1957 | McLaughlin et al. | 526/317 |
| 2,892,788 | 6/1959 | Stewart et al. | 526/317 |
| 3,194,777 | 2/1965 | Christenson et al. | 526/317 |
| 3,317,493 | 5/1967 | Selby | 526/317 |
| 3,577,517 | 5/1971 | Kabot et al. | 526/317 |
| 3,657,175 | 4/1972 | Zimmerman | 526/317 |
| 3,860,699 | 1/1975 | Kubota et al. | 424/47 |
| 3,940,351 | 2/1976 | Schlatter | 526/317 |
| 3,957,740 | 5/1976 | Blank et al. | 526/317 |
| 3,970,633 | 7/1976 | Miller et al. | 526/317 |

*Primary Examiner*—Herbert J. Lilling
*Attorney, Agent, or Firm*—Keil, Thompson & Shurtleff

[57] ABSTRACT

A process for the manufacture of copolymers by copolymerizing acrylic acid or methacrylic acid with esters of acrylic acid and methacrylic acid in the presence of polymerization initiators, in which methyl methacrylate, acrylic acid and/or methacrylic acid and a higher alkyl acrylate are copolymerized.

7 Claims, No Drawings

PROCESS FOR PREPARING COPOLYMERS OF ACRYLIC ACID OR METHACRYLIC ACID AND ACRYLIC AND METHACRYLIC ACID ESTERS

The present invention relates to a new process for the manufacture of copolymers of acrylic acid or methacrylic acid and esters of acrylic acid and methacrylic acid by free radical copolymerization of the said monomers at an elevated temperature.

It further relates to the use of the copolymers which have been manufactured in this way and then been neutralized, as an active principle (viz. a film-forming agent) in hair setting compositions.

For a considerable time, hair setting compositions based on various polymers have been used in cosmetics in order to impart a certain degree of firmness to human hair. These polymers include, for example, polyvinylpyrrolidone and vinylpyrrolidone/vinyl acetate, vinyl acetate/crotonic acid or maleic anhydride/vinyl ether copolymers. All these still suffer from disadvantages; either they are insufficiently soluble in the solvents from which they are to be applied, or they are too hygroscopic, ie. they tend to cause the hair to stick together, or they cannot be removed satisfactorily by combing the hair.

U.S. Pat. No. 3,577,517 and British Pat. No. 1,271,504 disclose hair setting compositions based, inter alia, on acrylic acid, methyl methacrylate and butyl acrylate. The polymerization process proposed in the said publications are characterized by the fact that they are carried out at below 100° C (reflux temperature) and at atmospheric pressure. However, the products obtained are again unsatisfactory in respect of their solubility in alcohols, methylene chloride or water/alcohol mixtures. Furthermore, they tend to cause the hair to stick together at relatively high atmospheric humidity. It is an object of the present invention to provide a film-forming agent which, though readily soluble in ethanol, isopropanol and methylene chloride, has a low water absorption and which, whilst providing a good stiffening effect, can be combed out without difficulty.

We have found, surprisingly, that this object is achieved by the process according to the invention, ie. in a process for the manufacture of copolymers by copolymerizing acrylic acid or methacrylic acid with esters of acrylic acid and methacrylic acid in the presence of free radical-forming initiators, wherein the improvement comprises copolymerizing — based on total weight of monomers (a) from 45 to 80% of methyl methacrylate,
(b) from 10 to 30% of one or more alkyl acrylates where alkyl is of 3 to 12 carbon atoms and
(c) from 10 to 25% of acrylic acid and/or methacrylic acid at from 140° to 300° C and at from 2 to 50 bars.

It is particularly surprising that the high content of methyl methacrylate and the relatively low content of higher acrylic esters does not detract from the solubility in alcohol, since a very recent publication (German Published Application DAS No. 2,161,909) discloses that a content of more than 40% by weight of methyl methacrylate and less than 40% by weight of acrylic esters gives alcohol-insoluble products. Accordingly, it was unexpected that a method of manufacture carried out at high temperatures and under superatmospheric pressure would not result in this disadvantage.

Whilst monomer (a) (methyl methacrylate) is a specifically defined starting material, the starting monomers (b) may be compounds such as n-propyl acrylate, n-butyl acrylate, n-hexyl acrylate or 2-ethylhexyl acrylate, n-octyl acrylate, n-decyl acrylate, n-dodecyl acrylate or mixtures of these. For the purposes of the present invention, n-butyl acrylate and 2-ethylhexyl acrylate are preferred. Suitable starting monomers (c) are acrylic acid, methacrylic acid and their mixtures, though the use of acrylic acid by itself is preferred.

The process is preferably carried out continuously. Suitable polymerization apparatus includes, for example, a pressure kettle, a pressure kettle cascade, a pressure tube or a pressure kettle with a downstream reaction tube equipped to act as a static mixer. Preferably, the monomers a, b and c are polymerized in at least two reaction zones in series. One zone may consist of a pressure-tight kettle and the other of a pressure-tight reaction tube, preferably a static mixer which can be heated. In the case of the last-mentioned embodiment, conversions of more than 98% are achievable.

The process according to the invention is carried out with the ratios of monomers defined above. The preferred amounts to use — based on total weight of the monomers — are from 60 to 75% of methyl methacrylate, from 10 to 20% of alkyl acrylate and from 10 to 25% of acrylic acid and/or methacrylic acid. The polymerization is preferably carried out at from 150° to 250° C, the preferred pressures being from 3 to 40 bars. The residence time of the monomers is in general from 3 to 60 minutes, preferably from 5 to 30 minutes.

The polymerization is initiated by conventional free radical-forming compounds, for example azo compounds, eg. azoisobutyronitrile, organic peroxides, eg. lauroyl peroxide, di-tert.-butyl peroxide, benzoyl peroxide or 4,4'-dinitrobenzoyl peroxide, or hydroperoxides, eg. tert.-butyl hydroperoxide. Advantageously, from 0.1 to 3% by weight, based on the weight of the monomers, of the free radical-forming compounds are used.

The polymerization may be carried out in the absence of solvents, ie. as a mass polymerization, or in the presence of solvents, eg. dioxane, ethanol, dimethylformamide, tetrahydrofuran, isopropanol, methylene chloride, toluene or ethylbenzene; it is not necessary to add regulators such as n-dodecylmercaptan or carbon tetrachloride.

After polymerization, and vaporization of any solvents used, a polymer melt is obtained, which is freed from residual monomers and any remaining traces of solvent, by treatment in a thin-film evaporator or by spray drying. In order to obtain odorless products it is advantageous subsequently to devolatilize the melt or free it from residual traces of monomers by treatment with steam.

In order to obtain a film-forming agent having optimum properties, the carboxyl groups can be neutralized, preferably to the extent of from 50 to 80%. Inorganic bases, eg. NaOH, KOH or ammonia, or, preferably, organic bases such as trimethylamine, triethylamine, tri-n-propylamine or tri-iso-propylamine, are used for this purpose. The use of aminoalcohols, such as 2-amino-2-methylpropanol (AMP) or 2-amino-2-methylpropanediol (AMPD) is particularly preferred.

The copolymers manufactured according to the invention have molecular weights of from 500 to 4,000, preferably from 800 to 2,500, and are excellent hair setting compositions which are distinctly superior to conventional acrylate resins in respect of their solubility in the solvents from which they are applied, their low hygroscopicity and their ease of removal by combing.

The Examples which follow illustrate the invention and are intended to show the excellent performance properties of the products of the invention over the most closely related prior art.

EXAMPLE 1

20 parts of methyl methacrylate, 5 parts of acrylic acid and 5 parts of n-butyl acrylate are dissolved in 5 parts of isopropanol which contain 0.5 part of di-tert.-butyl peroxide. The mixture is continuously fed to a pressure reactor with a downstream pressure tube comprising a static mixer, and is polymerized at 180° C under 30 bars. The mean residence time is 20 minutes. The solvent and the unconverted monomers are stripped off at from 15 to 25 mbars at about 180° C. To remove the last traces of volatile materials, the product is subjected to a final devolatilization in a thin film evaporator at 1.5 mbars and 220° C.

$\overline{M}_n^*$ = 1,210 acid number 126

*number-average mean molecular weight.

EXAMPLE 2

25 parts of methyl methacrylate, 8 parts of acrylic acid and 7 parts of ethylhexyl acrylate were polymerized by the method described in Example 1, without a solvent, at 165° C, and the product was worked up.

$\overline{M}_n^*$ = 1,530 acid number 202

*number-average mean molecular weight.

EXAMPLE 3

66 parts of methyl methacrylate, 17 parts of butyl acrylate and 17 parts of acrylic acid are polymerized by the method described in Example 1, but without a solvent.

$\overline{M}_n^*$ = 1,620 acid number 150

*number-average mean molecular weight.

For use in hair setting compositions the products obtained above are 75% neutralized with AMP.

COMPARATIVE EXAMPLE 1

(British Pat. No. 1,271,504, Example 4)

140 parts of methyl methacrylate, 40 parts of butyl acrylate and 20 parts of methacrylic acid were polymerized in the presence of 50 parts of methylene chloride as the solvent, and of 0.5 part of isopropyl peroxydicarbonate, in a reaction kettle under reflux cooling, in the course of 10 hours, during which a further part of initiator and a further 150 parts of methylene chloride were added. The solvent was then removed by distillation in vacuo. Before neutralization, the product had a mean molecular weight of 10,700. It was then 90% neutralized with a solution of sodium methylate in methanol.

COMPARATIVE EXAMPLE 2

(U.S. Pat. No. 3,577,517, Example 2)

110 parts of n-butyl acrylate, 10 parts of ethyl methacrylate, 30 parts of dodecyl methacrylate, 10 parts of dodecyl acrylate, 32 parts of acrylic acid and 8 parts of methacrylic acid were polymerized in the presence of 100 parts of ethanol, 100 parts of isopropanol and 4 parts of lauroyl peroxide in a 4-necked flask equipped with a reflux condenser, dropping funnel, thermometer and stirrer; a further 2 parts of initiator, dissolved in 50 parts of isopropanol, were then fed into the batch. The polymerization time was 4 hours and the reflux temperature was from 84° to 85° C.

The product was neutralized with 75 parts of KOH and 23 parts of morpholine in 110 parts of ethanol. This gave a solution having a solids content of 40%.

$\overline{M}_n^*$ = 4,600

*number-average molecular weight.

To compare the performance properties, the two above comparative materials and the copolymer obtained according to the invention, as described in Example 3, were employed.

The results of comparing the solubilities (3% solids) of the polymers which have not been neutralized can be seen in Table 1 below.

TABLE 1

| Solvent | Comparative Ex. 1 | Comparative Ex. 1 | Ex. 3 |
|---|---|---|---|
| 100% ethanol | -- | - | ++ |
| 96% ethanol | -- | - | ++ |
| isopropanol | -- | - | ++ |
| methylene chloride | - | + | + |
| ethanol/water, 1:1 (ratios by weight) | -- | -- | + |
| isopropanol/water, 1:1 (ratios by weight) | -- | - | ++ |
| isopropanol/methylene chloride, 1:1 (ratios by weight) | + | + | ++ |

-- = insoluble
- = slightly soluble
+ = soluble
++ = very readily soluble

The comparison of the solubilities, using products which have been 75% neutralized with 2-amino-2-methyl-propanol (AMP), can be seen in Table 2.

TABLE 2

| Solvent | Comparative Ex. 1 | Comparative Ex. 2 | Ex. 3 |
|---|---|---|---|
| 100% ethanol | + | + | ++ |
| 96% ethanol | + | + | ++ |
| isopropanol | -- | - | ++ |
| methylene chloride | - | ++ | ++ |
| ethanol/water, 1:1 | + | - | ++ |
| isopropanol/water, 1:1 | + | - | ++ |
| isopropanol/methylene chloride, 1:1 | ++ | ++ | ++ |

If the products are neutralized with KOH/morpholine, as described in U.S. Pat. No. 3,577,517, or with alkali metal alcoholates, as described in British Pat. No. 1,271,504, the solubilities, at 75% neutralization, of the comparative materials 1 and 2 appear even more unfavorable, whilst at 90% neutralization they show no improvement.

Table 3 below shows the water absorption of films produced from polymers 75% neutralized or 90% neutralized with sodium methylate.

TABLE 3

Water absorption at 75% relative atmospheric humidity after 7 days.

| Degree of neutralization | Water absorption (%) | | |
| | Comparative Example 1 | Comparative Example 2 | Example 3 |
|---|---|---|---|
| 75% | 24.6 | —* | 22.2% |
| 90% | 24.4 | —* | 22.1% |

*It was not possible to produce a satisfactory film with this material.

TABLE 4

Water absorption of films of polymers, 75% neutralized and 90% neutralized with AMP, at 75% relative atmospheric humidity.

| Degree of neutralization | Water absorption | | |
|---|---|---|---|
| | Comparative Example 1 | Comparative Example 2 | Example 3 |
| 75% | 9.4 | 9.5 | 7.4 |
| 90% | 10.2 | 10.4 | 10.0 |

Tables 3 and 4 show that in every case the copolymers manufactured according to the invention have a more advantageous water absorption, above all at the lower degree of neutralization, and as a result the hairstyle keeps better and the hair has less tendency to become tacky, since even a reduction in water absorption by as little as 0.5% results in the hairstyle withstanding an increase of 5% in the atmospheric humidity.

Some formulations for hair cosmetics are given below:

Hair spray 2.0% by weight of polymer from Example 3, 75% neutralized with AMP
38.0% by weight of ethanol or isopropanol
60.0% by weight of propellant gas 11/12 5050

Hair setting composition (a)

3.0% by weight of polymer from Example 3, 75% neutralized with AMP
40.0% by weight of isopropanol
57.0% by weight of water (b)

3.0% by weight of polymer from Example 3, 75% neutralized with AMP
30.0% by weight of isopropanol
67.0% by weight of water (c)

3.0% by weight of polymer from Example 3, 75% neutralized with AMP
50.0% by weight of ethanol
47.0% by weight of water.

These formulations result in the hair not becoming tacky even in humid air, and appearing very glossy and attractive in other respects also, whilst on the other hand the polymer is readily removable by washing or combing.

If, in the above formulations, the copolymer obtained as described in Example 3 is replaced by a copolymer obtained as described in Comparative Example 1 or 2, the hair becomes slightly tacky at atmospheric humidities above 70%.

We claim:

1. In a process for the manufacture of copolymers by copolymerizing acrylic acid or methacrylic acid with esters of acrylic acid and of methacrylic acid in the presence of initiators which form free radicals, the improvement which comprises copolymerizing — based on total weight of the monomers —
    (a) from 45 to 80% of methyl methacrylate,
    (b) from 10 to 30% of one or more alkyl acrylates where alkyl is of 3 to 12 carbon atoms and
    (c) from 10 to 25% of acrylic acid and/or methacrylic acid at temperatures of from 140° to 300° C, pressures of from 2 to 50 bars and with a monomer residence time sufficient to provide copolymers having molecular weights of from 500 to 4000.

2. A process as set forth in claim 1, wherein the copolymerization is carried out continuously.

3. A process as set forth in claim 1, wherein the copolymerization is carried out in the presence of organic solvents.

4. A process as set forth in claim 1, wherein the polymerization is carried out in the absence of regulators.

5. A process as set forth in claim 1, wherein, after copolymerization, the copolymers obtained are neutralized.

6. A process as set forth in claim 5, wherein after copolymerization, the copolymers are 50 to 80% neutralized.

7. A process as set forth in claim 1 wherein said monomer residence time is from about 3 to 60 minutes.

* * * * *